(12) United States Patent
Robinson et al.

(10) Patent No.: US 10,857,268 B2
(45) Date of Patent: Dec. 8, 2020

(54) SYSTEM AND METHOD FOR BODILY FLUID COLLECTION

(71) Applicant: KCI Licensing, Inc., San Antonio, TX (US)

(72) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 478 days.

(21) Appl. No.: 14/173,988

(22) Filed: Feb. 6, 2014

(65) Prior Publication Data

US 2014/0276497 A1   Sep. 18, 2014

Related U.S. Application Data

(60) Provisional application No. 61/780,305, filed on Mar. 13, 2013.

(51) Int. Cl.
*A61M 1/00* (2006.01)

(52) U.S. Cl.
CPC ........ *A61M 1/0056* (2013.01); *A61M 1/0001* (2013.01); *A61M 1/0088* (2013.01); *A61M 1/0096* (2014.02); *A61M 1/0098* (2014.02); *A61M 2205/75* (2013.01)

(58) Field of Classification Search
CPC .............. A61M 1/0056; A61M 1/0088; A61M 1/0096; A61M 1/0001; A61M 1/0098
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

International Searching Authority, Communication Relating to the Results of the Partial International Search for PCT/US2014/015160, dated Jul. 29, 2014.

(Continued)

*Primary Examiner* — Tatyana Zalukaeva
*Assistant Examiner* — Jessica R Arble (57) ABSTRACT

A bodily fluid collection system may include a canister fluidly connected to a dressing at a tissue site through an inlet. The canister may also be fluidly connected to a reduced pressure source through an outlet. At least a portion of the wall of the canister may be a membrane and may have the open edge of a flexible bag container fixed to the canister surrounding the perimeter of the membrane. The flexible bag may contain an osmotic agent capable of drawing absorbent from bodily fluid in the canister through the membrane and into the flexible bag.

34 Claims, 3 Drawing Sheets

(56) References Cited

U.S. PATENT DOCUMENTS

| | | |
|---|---|---|
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,241,733 A * | 12/1980 | Langston ............... A01N 35/02 604/322 |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,284,621 A * | 2/1994 | Kaufman ............... A61L 11/00 206/524.6 |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2001/0036422 A1 * | 11/2001 | Lin ............... A61L 2/14 422/28 |
| 2002/0077661 A1 | 6/2002 | Saadat |
| 2002/0082699 A1 * | 6/2002 | Ward ............... A61F 2/441 623/17.16 |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0006321 A1 * | 1/2004 | Cheng ............... A61F 5/44 604/349 |
| 2006/0079852 A1 | 4/2006 | Bubb et al. |
| 2007/0265585 A1 * | 11/2007 | Joshi ............... A61M 1/0015 604/313 |
| 2007/0265586 A1 * | 11/2007 | Joshi ............... A61M 1/0031 604/313 |
| 2011/0257613 A1 * | 10/2011 | Locke ............... A61F 13/0206 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0596132 A1 | 5/1994 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | WO2013028785 A1 | 2/2013 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, (56) References Cited

OTHER PUBLICATIONS edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

SYSTEM AND METHOD FOR BODILY FLUID COLLECTION

RELATED APPLICATION

This application claims the benefit, under 35 USC § 119(e), of the filing of U.S. Provisional Patent Application Ser. No. 61/780,305, entitled "SYSTEM AND METHOD FOR BODILY FLUID COLLECTION," filed Mar. 13, 2013, which is incorporated herein by reference for all purposes.

FIELD OF THE INVENTION

This disclosure relates generally to tissue treatment systems and more particularly, but without limitation, to systems and methods for collecting bodily fluids.

BACKGROUND

Clinical studies and practice have shown that providing a reduced pressure in proximity to a compromised tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue.

Wound fluids, also known as exudates, are generally collected in a canister for disposal or analysis. Wound fluid primarily consists of plasma in addition to red and white blood cells, platelets, bacteria, and a variety of proteinaceous material. Plasma consists primarily of saline. In clinical practice, it is desirable that canisters are sized large enough to obviate the need for frequent replacement even when used in the treatment of wounds generating a high volume of exudate. Conversely, it is also desirable that the canister is not so bulky that the canister consumes too much storage space or unnecessary resources for hazardous waste disposal of canisters filled with potentially infectious wound fluid. In the home healthcare environment, storage and disposal issues are more pronounced. Caregivers in the home environment must also supply empty canisters and dispose of filled canisters. Minimizing this burden and potential accidents resulting from the disposal of filled containers is useful as well as more cost-effective.

SUMMARY

In an illustrative embodiment, a fluid collection system may include a fluid collection device with an inlet and an outlet, and a wound dressing fluidly connected to the inlet of the fluid collection device via a conduit. The fluid collection device may include a support member comprising a wall with an opening and an interior chamber defined by the wall of the support member. The support member may be a canister. The wall of the canister may be configured to be sufficiently rigid such that when a reduced pressure is applied to an outlet, the wall of the canister remains sufficiently fixed thereby imparting the reduced pressure to the inlet and then to the wound dressing, pulling bodily fluid into the canister.

The fluid collection device may also include a container enveloping the opening of the wall of the canister. The opening may contain a grid, lattice, frame, or perforated section over which a membrane is fixed. The membrane may be a semi-permeable membrane, a permeable membrane, a selectively permeable membrane, a selective membrane, or a partially permeable membrane. The membrane may be configured to selectively permit small molecules such as water to readily pass through and yet prevent the passage of larger molecules such as sugars, proteins, or microorganisms such as bacteria, viruses, and fungi. In this manner, selected components of the bodily fluid in the canister may pass through the membrane, entering the container.

An osmotic agent may be disposed in the container to establish an osmotic pressure gradient across the membrane. The osmotic pressure gradient may pull solvent molecules from the bodily fluid in the canister across the membrane and into the container. The container may be made of a flexible material, allowing the volume of the container to increase as the selected components of the bodily fluid are drawn from the canister into the container. A heating element, a stirring mechanism, or both may be located with the canister to accelerate the transit time of solvent molecules through the membrane.

An antimicrobial agent may be placed in the container or in the canister or both to reduce the bioburden of the bodily fluid collected in the fluid collection device. The container may comprise a mechanism configured to evacuate fluid from the container. When the container becomes filled with fluid it may be useful to evacuate the bodily fluid to enable the continued use of the system. Following the medical practice of standard precautions, also generally known as universal precautions, caregivers strive to avoid contact with bodily fluids. Extracted bodily fluids are considered to be medical waste and as such are often incinerated. To the extent that sterile saline can be separated from the bodily fluid, the volume of medical waste required to be disposed would be reduced. In a home health care environment, this medical waste reduction may be especially important because of the limited resources available in that environment. The container may comprise a mechanism configured to introduce fluid into the container to mix with the solid or crystalline osmotic agent, generating the needed solution to start the osmotic process.

In another illustrative embodiment, a fluid collection device for collecting bodily fluids from a tissue site using reduced pressure may include a support member, a container, a membrane, and an osmotic agent. The support member may have an inlet adapted to be in fluid communication with a dressing disposed at the tissue site, and an outlet adapted to be in fluid communication with a source of reduced pressure. The container may be coupled to the support member, and may be in fluid communication with the inlet and the outlet of the support member. The membrane may be disposed between the container and the support member, and the osmotic agent may be disposed within the container.

In another illustrative embodiment, a fluid collection system may include a dressing, a canister, a container, and a hypertonic solution. The dressing may be adapted to be in communication with a tissue site. The canister may be in fluid communication with the tissue site and in fluid communication with a reduced pressure source. A portion of the canister may comprise a membrane, and the canister may be adapted to accept bodily fluid from the tissue site. The container may have an opening with an edge. The edge of the container may be mated to the canister surrounding the membrane. The hypertonic solution may be located within the container. The hypertonic solution may be adapted to draw absorbent from the bodily fluid in the canister through the membrane.

In another illustrative embodiment, a method for reducing the volume of bodily fluid collected may include creating a reduced pressure within a canister to draw bodily fluid from a tissue site to the canister through an inlet, wherein the canister has an outlet and a liquid-air separator associated with the outlet. Further, the method may include osmosing absorbent from the bodily fluid in the canister into a container attached to the canister, and removing the absorbent from the container.

In another illustrative embodiment, a bodily fluid collection device may include a canister, a membrane, a variable volume container, and an osmotic agent. The canister may include an inlet for fluid communication with a dressing at a tissue site, an outlet for fluid communication with a reduced pressure source, and a chamber defined by a wall. The wall may include a lattice having a surrounding edge. The membrane may be adhered to the lattice. Further, the membrane may have a textured surface and may be operable to prevent microorganisms from traversing therethrough. The variable volume container may be affixed to the wall of the chamber and may encompass the surrounding edge of the lattice. Further, the variable volume container may be in communication with the canister through said membrane. The variable volume container may also include a valve in communication with the atmosphere. The osmotic agent may be located within the container. Further, the osmotic agent may be combined with a water soluble bonding agent.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof. These embodiments are described in sufficient detail to enable those skilled in the art to practice the subject matter of this disclosure. Other embodiments may be utilized, and logical, structural, mechanical, electrical, and chemical changes may be made without departing from the scope of this disclosure. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the tissue site is located. The reduced pressure may also be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure may be maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, ligaments, or parenchymatous tissue. The term "tissue site" may further refer to areas of any tissue that are not necessarily wounded or defective, but are instead areas in which it is desired to add or promote the growth of additional tissue.

Figure 1:
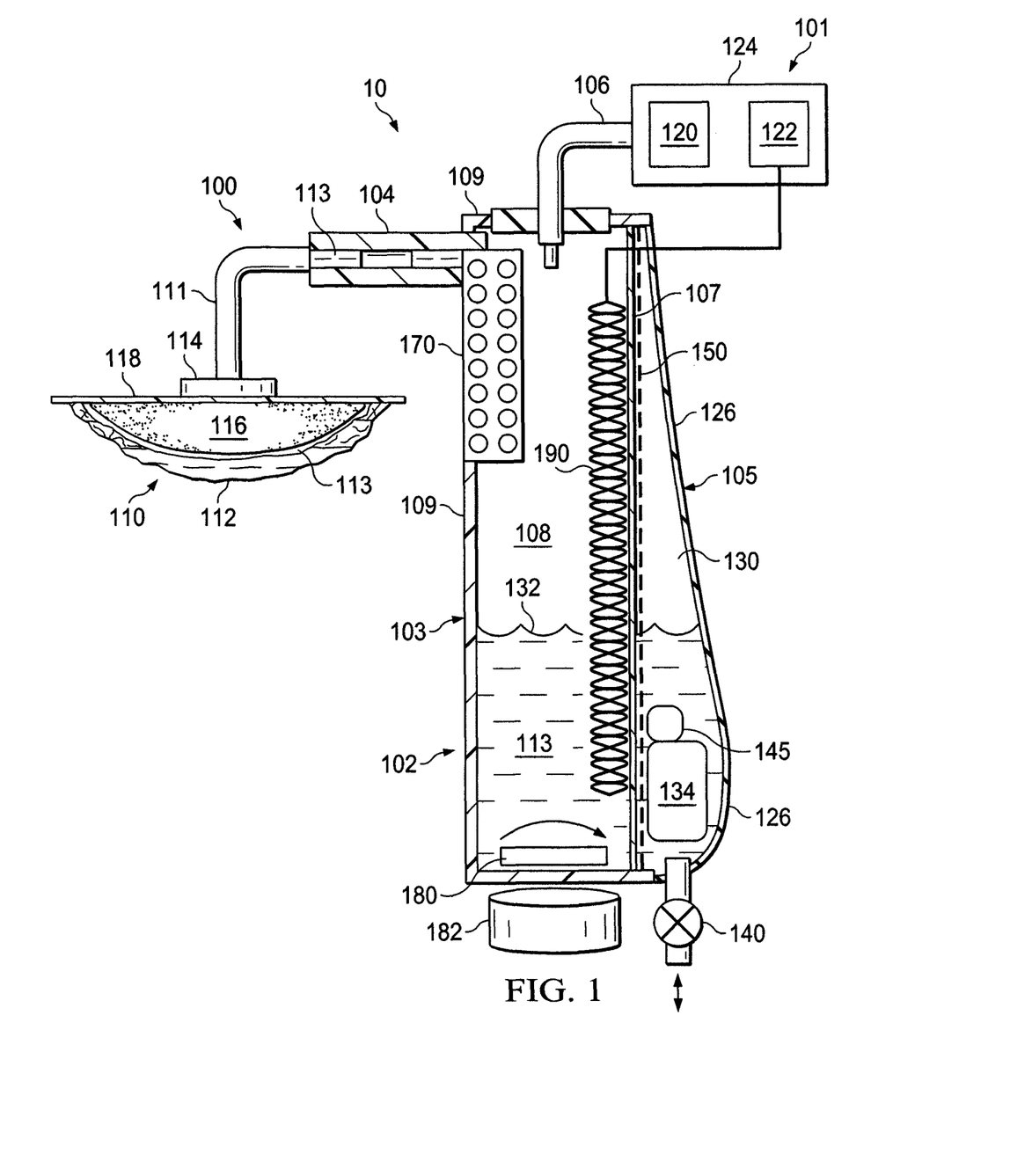
FIG. 1 depicts a sectional, side view of a fluid collection system having a canister, a container, a membrane, and an osmotic agent according to a first illustrative embodiment.
Figure 2:
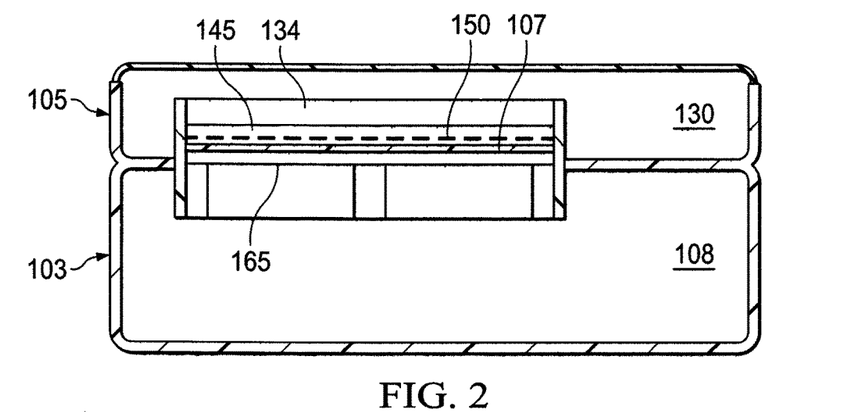
FIG. 2 depicts a sectional, top view of the fluid collection system of FIG. 1 further including a lattice adjacent the membrane.

Referring to FIGS. 1 and 2, a reduced pressure treatment system 10 may comprise a fluid collection system 100 and a reduced pressure system 101 according to one illustrative embodiment. The fluid collection system 100 may comprise a fluid collection device 102 that may include a support member having an inlet 104 and an outlet 106, a container 105 fluidly coupled to the support member, and a membrane 107 disposed between the support member and the container 105. The support member in a first embodiment may be a canister 103 comprising walls 109 and an opening that define a chamber 108 within the walls 109. The inlet 104 and outlet 106 of the canister 103 are in fluid communication with the chamber 108. The fluid collection system 100 may further comprise a wound dressing 110 fluidly coupled to the inlet 104 of the fluid collection device 102 via a conduit or tube 111 containing at least one lumen for the transmission of fluids, both gaseous and liquid.

The wound dressing 110 may comprise a tube adapter 114 adapted to be fluidly coupled to the tube 111, and a distribution manifold 116 fluidly coupled to the tube adapter 114 and adapted to be positioned proximate the tissue site 112 for distributing reduced pressure to the tissue site 112. The wound dressing 110 may further comprise a drape 118 adapted to cover the distribution manifold 116 for providing a substantially airtight seal over the tissue site 112 to maintain the reduced pressure at various desired levels. The drape 118 may include an adhesive seal (not shown) capable of maintaining the reduced pressure at various levels, and holding the wound dressing 110 in place over the tissue site 112. The distribution manifold 116 may be a bioabsorbable or bioinert material capable of distributing reduced pressure to the tissue site 112. In one embodiment, the distribution manifold 116 may be an open-cell, reticulated foam comprising, for example, a polyurethane material. The wound dressing 110 may deliver reduced pressure to a tissue site 112 to provide therapeutic treatment to the tissue site 112 and collect exudates and bodily fluids 113 from the tissue site 112. Delivery of reduced pressure to the tissue site 112 may also encourage new tissue growth by maintaining drainage of bodily fluids 113 from the tissue site 112, increasing blood flow to tissue surrounding the tissue site 112, and compressing the distribution manifold 116 into the tissue site 112 to create microstrain.

The reduced pressure system 101 may comprise a reduced pressure source 120 and a processing unit 122. The reduced pressure source 120 may be fluidly coupled to the outlet 106 of the canister 103 for providing reduced pressure to the chamber 108 of the canister 103. The reduced pressure source 120 may be a reduced pressure or vacuum pump driven by a motor. In another embodiment, the reduced pressure source 120 may be a manually-actuated pump such as a compressible bellows pump. In still another embodiment, the reduced pressure source 120 may be a wall suction port either with or without a separate pressure regulator.

The reduced pressure source 120 and the processing unit 122 may both be housed within a reduced pressure treatment unit 124 which may also contain sensors, processing units, alarm indicators, memory, databases, software, display units, and user interfaces that further facilitate the application of reduced pressure treatment to the tissue site. In one example, a sensor (not shown) may be disposed at or near the reduced pressure source 120 to determine a source pressure level generated by the reduced pressure source. The sensor may communicate with the processing unit 122 that monitors and controls the reduced pressure delivered by the reduced pressure source 120.

The canister 103 may be a unitary housing having a substantially rectangular or box-like shape wherein the walls 109 may be substantially rigid. In some embodiments, the canister 103 and consequently the internal chamber 108 may have other shapes that are cylindrical, cubical, spherical or parabolic. The membrane 107 may be coupled to the walls 109 of the canister 103 and sized to cover the opening of the canister 103 to close the chamber 108 of the canister 103. If the opening of the canister 103 is substantially flat, then the membrane 107 may also be substantially flat. In other embodiments, the opening of the canister 103 formed by the walls 109 of the canister 103 may create a curved surface in which case the membrane may take on a shape substantially similar to the curved surface of the opening of the canister 103. The membrane 107 may take on a variety of shapes depending on the structure of the support member or the canister 103 as will be described in more detail below in conjunction with FIG. 4.

The opening of the canister 103 may be flat or structured to have a lip portion for engaging or coupling to the container 105 when assembled. The container 105 may be permanently or detachably coupled to the walls 109 of the canister 103 to cover the opening of the canister 103. The container 105 may be coupled to the canister 103 by a variety of techniques including, for example, welding, bonding, pressure fitting, or by use of any other attachment means. The container 105 may also comprise walls 126 and an opening that define a cavity 130 within the walls 126. Because the membrane 107 covers the opening of the canister 103, the container 105 envelops the membrane 107 when coupled to the canister 103 such that the membrane 107 effectively separates or divides the canister chamber 108 from the cavity 130.

The cavity 130 essentially takes on the shape of the container 105. For example, the container 105 may be a flexible bag that consequently has a variable or expandable cavity 130. The flexible bag may be configured with extra folds or pleats of material to permit it to expand in volume as needed when fluids flow into the cavity 130. The flexible bag may have elastic characteristics to permit it to stretch as needed during use. The container 105 may be constructed of a plastic material that allows moisture vapor to transfer from within the container 105 to the atmosphere. This plastic material may be a hydrophilic polymer such as polyurethane, a nylon, a cellulose derivative, or any other material that is capable of retaining liquid while allowing the passage of vapor.

The membrane 107 may permit transmission of small molecules while blocking the movement of larger molecules, cells, or microorganisms. The membrane 107 may be selected to specific needs based on various characteristics such as the pore size, geometry, or material of manufacture. By way of a non-limiting example, the membrane 107 may have a pore size of 0.1 μm which may limit the passage of certain bacteria such as Staphylococcus Aureus which tends to be larger than 0.5 μm. The membrane 107 may be constructed of a variety of materials including, but not limited to, cellulose acetate, polyethylene, polyamide, or polyvinyl chloride. The membrane 107 may be flat, textured, or folded to provide a greater surface area as needed. For example, the membrane 107 may be corrugated to provide a greater surface area than a flat rectangular surface would provide. The membrane 107 may comprise an uneven surface to provide a greater surface area than a similarly sized flat rectangular surface would provide. The increased surface area of the membrane 107 enhances its efficacy for filtering molecules from the fluid. The membrane 107 may be coated with a hydrophilic agent.

The chamber 108 of the canister 103 fills with bodily fluid 113 that flows from a body through the inlet 104 as a result of reduced pressure being applied to the tissue site 112. An osmotic agent 134 may be disposed within the cavity 130 of the container 105 to generate an osmotic pressure gradient between the bodily fluid 113 in the chamber 108 of the canister 103 and the cavity 130 of the container 105 across the membrane 107. The bodily fluid 113 in the chamber 108 may be a hypotonic fluid, and the fluid in the cavity 130 of the container 105 may be a hypertonic fluid. Solvent molecules may move across the membrane 107 from a less concentrated solute to a more concentrated solute. As such, a variety of compounds may be used as the osmotic agent 134 to generate an osmotic gradient across the membrane 107. In one embodiment, the osmotic agent 134 may be 10 grams of sodium chloride. In one embodiment, the hypertonic fluid in the cavity 130 of the container 105 may be 10 grams of sodium chloride mixed in 100 ml of water generating an osmotic pressure gradient of about 75.5 atmospheres relative to the approximately normal saline hypotonic fluid in the chamber 108 of the canister 103. In another embodiment, the osmotic agent 134 may be 10 grams of sucrose. In another embodiment, the hypertonic fluid in the cavity 130 of the container 105 may be 10 grams of sucrose mixed in 100 ml of water generating an osmotic pressure gradient of about 7.1 atmospheres relative to the approximately normal saline hypotonic fluid in the chamber 108 of the canister 103. Examples of the osmotic agent 134 include sodium salts, potassium salts, ammonium salts, and sugars.

Although the osmotic agent 134 is shown as a specific shape, the osmotic agent 134 may be configured as a solid, particles, or a concentrated solution. In one embodiment, the osmotic agent 134 may be a solid material positioned adjacent the membrane 107. The osmotic agent 134 be temporarily adherent to the membrane 107 or may be affixed or otherwise permanently attached to the surface of the membrane 107. The osmotic agent 134 may be in a solution to initiate the osmotic diffusion process. When the osmotic agent 134 is used in the form a of a concentrated solution, the concentration of the solute may be sufficiently higher than the expected concentration in the bodily fluid to generate a net flow of absorbent 132 from the hypertonic bodily fluid to the hypotonic osmotic solution.

When the osmotic agent 134 is used in a solid form, the osmotic agent 134 may be combined with a disintegrant, such as an excipient, added to aid in the breakup of a compacted form when it is placed into a fluid. A variety of materials may be used as the disintegrant including potato starch, corn starch, polyvinylpyrrolidone, and microcrystalline cellulose. Other materials may be suitable without departing from the scope of the exemplary embodiments disclosed herein. When the osmotic agent 134 is used in solid form, a vessel (not shown) holding a liquid may be located within the container 105. The vessel may be configured to be punctured thereby releasing liquid into the container 105 and contacting the osmotic agent 134 to generate the hypertonic solution. When the osmotic agent 134 is used in a solid form, the osmotic agent 134 may be combined with a water soluble bonding agent, such as an excipient, added to aid in the breakup of a compacted form when it is placed into a fluid. A variety of materials may be used as the water soluble bonding agent including polyvinyl alcohol resins, polymers, and carboxymethylcellulose.

The container 105 may further comprise a valve 140 having an open and closed position, wherein the open position provides fluid communication with the cavity 130 of the container 105 and the closed position prevents fluid communication with the cavity 130. When the valve 140 is in the closed position, the hypotonic osmotic solution including the absorbent 132 is sealed within the cavity 130 of the container 105. When the valve 140 is in the open position, the contents of the container 105 including the absorbent 132 may be drained or evacuated from the cavity 130 of the container 105. In some embodiments, in the open position, the valve 140 may be used for the introduction of fluid into the cavity 130 such that the fluid contacts the osmotic agent 134. For example, when the osmotic agent 134 is used in a solid form, a disintegrant fluid may be introduced into the cavity 130 to dissolve the solid osmotic agent 134.

An antimicrobial agent 145 may be disposed in the cavity 130 of the container 105. The antimicrobial agent 145 may take a variety of forms. Both the antimicrobial agent 145 and the osmotic agent 134 may be combined in a solid form. The antimicrobial agent 145 may also be formulated in particles or in solution. Many antimicrobial agents are known including polyhexanide, a fast acting, broad spectrum synthetic compound that binds to and disrupts the cell membrane. Other available preparations of polyhexanide include Prontosan® (B-Braun Medical) and Decontaman (Dr. Schumacher GMBH). The antimicrobial agent 145 can effect a bioburden logarithmic reduction of greater than one or, more preferably, greater than three. It can be appreciated that any other broad spectrum antimicrobial agent could be used to also accomplish a similar bioburden reduction. The antimicrobial agent 145 may also be coated onto the inner surface of the container 105 such that it will be in contact with the absorbent 132 that has been removed from the bodily fluid via the osmotic process. Alternately, the antimicrobial agent 145 may be disposed in the chamber 108 of the canister 103.

The canister 103 may also include a lattice or screen 150 coupled to the walls 109 of the canister 103 and adjacent the membrane 107 in part to provide support to the membrane 107. The membrane 107 may be held in a fixed position by simply being positioned inside the chamber 108 of the canister 103 with the screen 150 being positioned within the cavity 130 of the container 105. In another embodiment, the membrane 107 may be coupled to the screen 150 when the screen 150 is positioned within the chamber 108 of the canister 103 so that the membrane 107 adheres to the screen 150 without being pulled away by the osmotic pressure gradient. The screen 150 may be formed with a flat surface or formed in the same shape as the membrane 107. Other embodiments of the screen 150 include channels, creases, grooves, pleats, ribs, and textures to facilitate the flow of fluids through the membrane 107. The canister 103 may also include a hydrophobic agent such as a hydrophobic filter 165 (shown only in FIG. 2) coupled to the walls 109 of the canister 103 and adjacent the membrane 107.

The canister 103 may also include a large-porosity filter 170 positioned in fluid communication between the inlet 104 and the chamber 108 to trap larger pieces of fibrin or other solids flowing in the bodily fluid 113 from contacting and plugging the membrane 107. The large-porosity filter 170 may comprise an open-cell polyurethane foam having relatively large porosity including pores with an average diameter larger than about 0.05 mm and smaller than about 10 mm, and preferably between about 0.2 mm and about 2 mm. As bodily fluid 113 is drawn into the fluid collection device 102, the large-porosity filter 170 traps the solid material that has a diameter larger than the pores of the large-porosity filter 170. The large-porosity filter 170 may collect particles passively by relying simply on the size of the particle and the size of the pore, but may also collect particles actively by employing a large-porosity filter 170 formed with or coated by a charged material to adsorb proteins such as those commonly found in bodily fluids. In some embodiments, the large-porosity filter 170 may be positioned within the chamber 108 of the canister 103 between the inlet 104 and the membrane 107. The large-porosity filter 170 may be disposed within the chamber 108 so that the bodily fluid 113 drops onto the large-porosity filter 170 when the bodily fluid 113 flows into the chamber 108. In this manner, the large-porosity filter 170 may be larger and able to trap more solid material either within the filter or in that portion of the chamber 108 between the large-porosity filter 170 and the inlet 104.

The canister 103 may also include a magnetic stirring system comprising a magnetic stir bar 180 located in the chamber 108 of the canister 103 and a magnetic drive unit 182 positioned outside the canister 103 that magnetically rotates the magnetic stir bar 180 as indicated by the arrow. The stirring action of the stir bar 180 facilitates the osmotic action by accelerating movement of the bodily fluid 113 through the membrane 108. The magnetic drive unit 182 may also be part of the reduced pressure system 124 and controlled by the processing unit 122. The stir bar 180 may be sealed inside the canister 103 and disposed of with the canister 103. Other means of rotating the magnetic stir bar 180 are equally suitable including the use of fixed electromagnets. Similarly, other means of agitating or stirring the bodily fluid in the canister 103 may be used with equal effect, including a motor connected shaft penetrating the wall of the canister 103 through a bearing and connected to a propeller or rod within the chamber 108 or an orbital shaker unit on which the canister 103 is positioned.

The canister 103 may also include a heating element 190 positioned within the chamber 108 and proximate the membrane 107. The heating element 190 may be an integral component of the canister 103 controlled by the processing unit 122 and utilized when needed. The heating element 190 may also be energized by a power source (not shown) located external to the canister 103 and contained within the reduced pressure system 124. The heating element 190 may be operable between about 20° C. and about 60° C., and preferably between about 25° C. and about 45° C. In other embodiments, the bodily fluid 113 may be heated by a source of radiant energy (not shown) located inside or outside the canister 103. The source of radiant energy may be, for example, an electromagnetic field or a light source such as, for example, one or more light emitting diodes (LEDs).

Figure 3A:
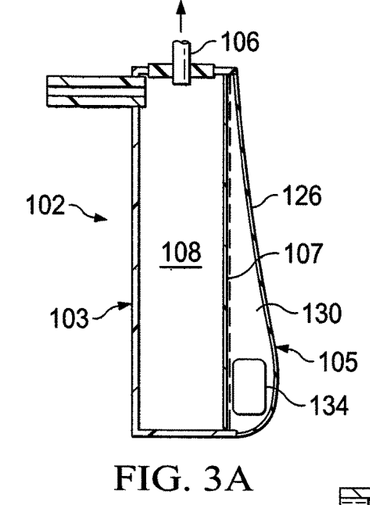
FIGS. 3A-3C depict the expansion of the container of the fluid collection system of FIG. 1 resulting from the flow of fluid to the container in an illustrative embodiment.
Figure 3B:
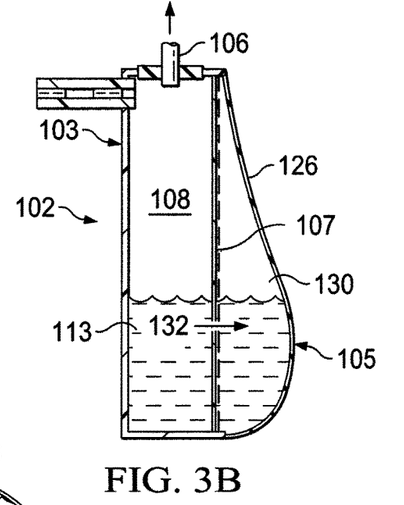
Figure 3C:
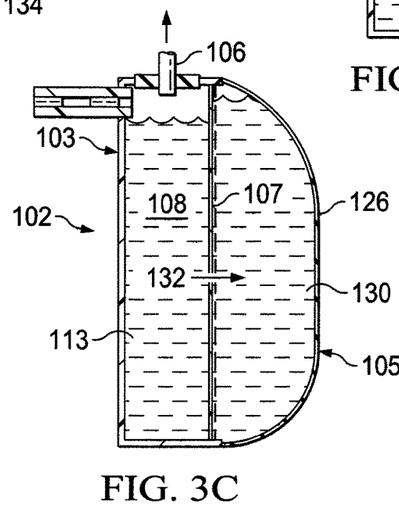

Referring to FIGS. 3A-3C, the fluid collection device 102 is shown in operation wherein the walls 126 of the container 105 are flexible as described above. The walls 126 of the container 105 are shown as expanding from an empty state in FIG. 3A to a partially filled state in FIG. 3B and a substantially filled state in FIG. 3C. More specifically, FIG. 3A shows the fluid collection device 102 prior to use with the osmotic agent 134 located in the cavity 130 of the container 105 before any bodily fluid 113 enters into the chamber 108 of the canister 103. FIG. 3B shows the osmotic gradient induced migration of the absorbent 132 from the bodily fluid 113 in the chamber 108 of the canister 103 through the membrane 107 into the cavity 130 of the container 105 which expands to hold increasing quantities of the absorbent 132. Finally, FIG. 3C shows the container 105 substantially filled with absorbent 132 from the bodily fluid 113 after the container 105 has expanded dramatically to hold a large quantity of the absorbent 132. As can be seen, the flexibility of the walls 126 of the container 105 enhances the capability of the fluid collection device 102 to collect bodily fluids 113 over an extended period of time without having to replace the entire device or the container 105, if detachable.

Figure 4:
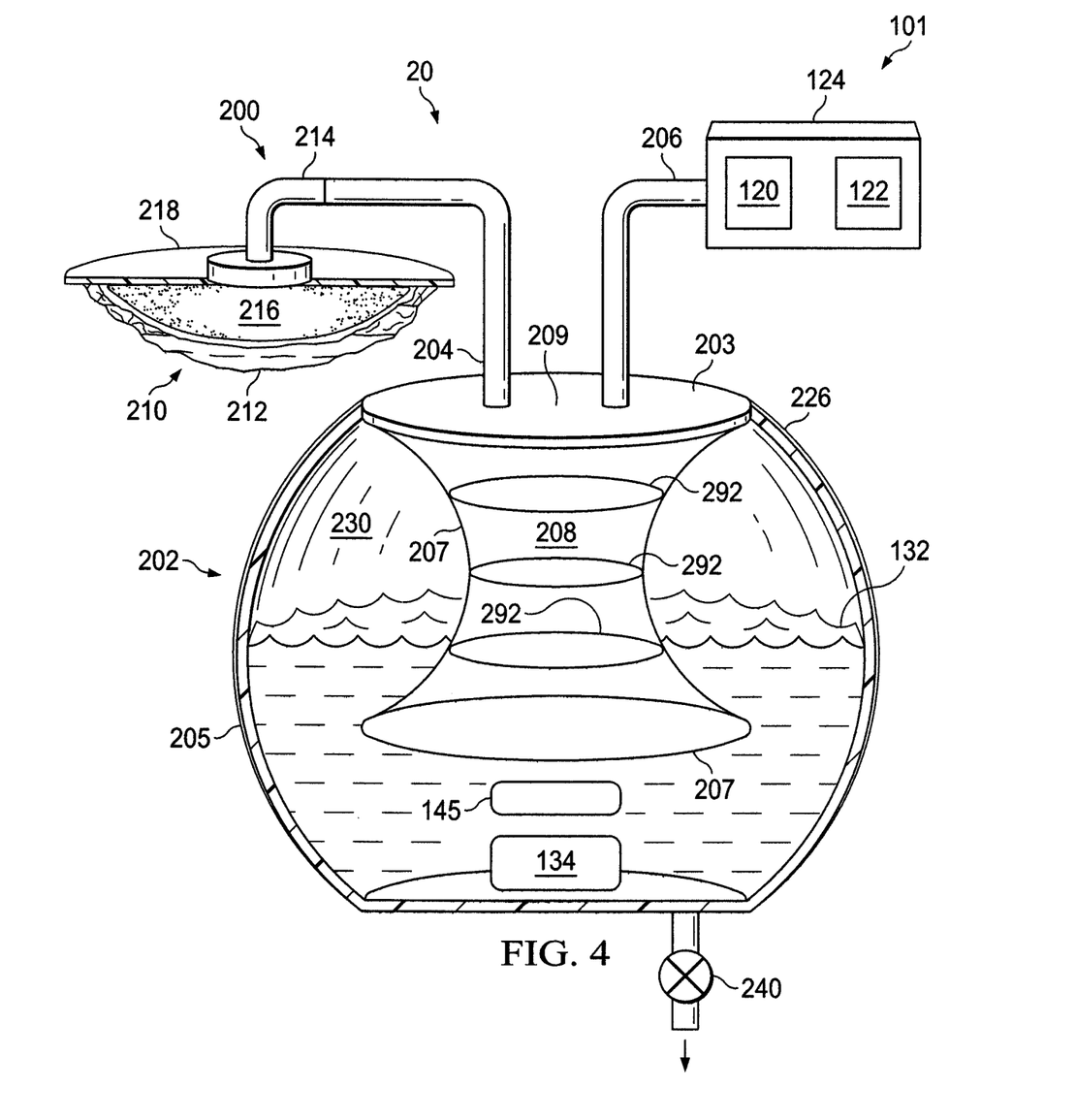
FIG. 4 depicts a sectional, side view of a fluid collection system having a canister, a container, and an osmotic agent according to a second illustrative embodiment.

Referring now to FIG. 4, a reduced pressure treatment system 20 may comprise a fluid collection system 200, and the reduced pressure system 101 according to another illustrative embodiment. The fluid collection system 200 may comprise a fluid collection device 202 that may include a support member having an inlet 204 and an outlet 206, a container 205 fluidly coupled to the support member, and a membrane 207 disposed between the support member and the container 205. The support member in a second embodiment may be a lid 203 comprising a single wall 209. The container 205 may include walls 226 and an opening that define a cavity 230 within the walls 226. The membrane 207 may include walls and an opening that define a cavity or chamber 208 accessible through the opening in the membrane 207. The inlet 204 and the outlet 206 of the lid 203 may be in fluid communication with the cavity 230 and the chamber 208. The fluid collection system 200 may further comprise a wound dressing 210 fluidly coupled to the inlet 204 of the fluid collection device 202 via a tube 214. The fluid collection system 200 may otherwise be substantially similar to the fluid collection system 100 except for the fluid collection device 202, which functions in a similar fashion to the fluid collection device 102. The primary difference between the two is that the membrane 207 defines the chamber 208 when the lid 203, being substantially flat in some embodiments, is used as the support member, rather than the canister 103 defining the chamber 108 when the canister 103 is used as the support member.

The membrane 207 may be self-supporting in one embodiment, or may be supported by one or more reinforcing rings 292 affixed to the membrane 207 to provide volumetric structure to the membrane 207. The opening of the membrane 207 may be coupled to at least a portion of the lid 203 that includes the inlet 204 and the outlet 206. The container 205 may also be coupled to the lid 203 and enclose the entire outer surface of the membrane 207. The container 205 may be a flexible bag similar to the container 105 so that the container 205 is also capable of expanding to retain more bodily fluid 113 as described above. The container 205 may be configured with extra folds or pleats of material to facilitate additional expansion as needed to collect larger quantities of fluids. Likewise, the container 205 may have elastic characteristics to permit it to stretch as needed during use. The container 205 may also include a valve 240 mounted proximate the base of the container 205 that functions in a substantially similar fashion as the valve 140. The osmotic agent 134 may be positioned within the cavity 230 of the container 205 to generate an osmotic pressure gradient between the hypotonic fluid within the chamber 208 and the hypertonic fluid within the cavity 230 of the container 205 across the membrane 207 in a fashion substantially similar to the fluid collection device 102 as described above.

According to an illustrative embodiment, a method for reducing the volume of bodily fluid collected in a canister may include the steps of creating a reduced pressure within a canister such that bodily fluid is drawn into the canister, osmosing absorbent from the bodily fluid in the canister into a container attached to the canister, and removing the absorbent from the container. The reduced pressure may be generated in the canister through an outlet in the canister to which a reduced pressure source may be attached. The bodily fluid may be drawn into the canister from a tissue site through an inlet in the canister. The canister may comprise a liquid-air separator associated with the outlet of the canister. The absorbent may be removed from the container through a valve. The method may also comprise reducing the bioburden of the absorbent within the container.

The illustrative embodiments described herein may be used with reduced pressure treatment systems of any type, shape, or size, and similarly, with canisters of any type, shape, or size. The location of the inlet, outlet, membrane, and flexible bag may also vary depending upon the particular collection system design. Similarly, the geometry of the membrane may be modified as necessary to conform to the contours or configuration of the canister. Similarly, the location of the means to withdraw the collected absorbent may also vary depending upon the particular collection system design.

The subject matter of this disclosure is described in the context of several non-limiting, illustrative embodiments. As indicated above, various changes and modifications may be made to these illustrative embodiments without departing from the scope of this disclosure as defined by the appended claims. Further, the features described above in connection with any one embodiment may be applicable to any other embodiment.

We claim:
1. A fluid collection device for collecting bodily fluids from a tissue site using reduced pressure, the fluid collection device comprising:
   a support member having an inlet adapted to be in fluid communication through a tube connected to a dressing disposed at the tissue site and an outlet adapted to be in fluid communication with a source of reduced pressure;
   a chamber in fluid communication with the inlet and the outlet;

a container coupled to an exterior portion of the support member and defining a variable volume cavity that is in fluid communication with the inlet and the outlet of the support member;

a membrane disposed between the variable volume cavity and the chamber, and wherein the membrane is configured to permit the passage of water-sized molecules; and an osmotic agent disposed within the variable volume cavity, wherein the osmotic agent is configured to generate an osmotic pressure gradient across the membrane to pull the water-sized molecules from the bodily fluids, across the membrane, and into the variable volume cavity.

2. The device of claim 1, wherein the support member is a canister comprising walls and an opening that define the chamber within the walls of the canister, and wherein the membrane covers the opening of the canister.

3. The device of claim 2, wherein a porous material is contained within said chamber of said canister, said porous material positioned in a path of fluid entering said chamber.

4. The device of claim 2, said canister further comprising a stirring mechanism whereby fluid collected in said canister will be kept in motion.

5. The device of claim 1, wherein the support member is a lid, and wherein the membrane comprises walls and an opening that defines the chamber within the walls of the membrane, the membrane being enclosed by the container.

6. The device of claim 1, wherein said container is a bag.

7. The device of claim 1, wherein an opening of said container is removably affixed to the chamber.

8. The device of claim 1, wherein said container further comprises a valve.

9. The device of claim 1, wherein a vessel holding a fluid is positioned within said container, said vessel configured to release said fluid into said container contacting said osmotic agent.

10. The device of claim 1, wherein at least a portion of a wall of said support member comprises a lattice on which said membrane is supported.

11. The device of claim 1, wherein said membrane is operable to prevent microorganisms from traversing from said support member into said container.

12. The device of claim 1, wherein at least a portion of a surface of said membrane is textured.

13. The device of claim 1, wherein at least a portion of a surface of said membrane is coated with a hydrophilic agent.

14. The device of claim 1, wherein said osmotic agent is combined with a disintegrant.

15. The device of claim 1, wherein said osmotic agent is combined with a water soluble bonding agent.

16. The device of claim 1, wherein said membrane is at least partially coated with said osmotic agent.

17. The device of claim 1, further comprising an antimicrobial agent located within said container.

18. The device of claim 1, further comprising an antimicrobial agent located within the chamber.

19. The device of claim 1, further comprising a heating element.

20. The device of claim 1, further comprising a liquid-air separator associated with the outlet.

21. The device of claim 1, wherein the inlet and the outlet are separately coupled to the support member.

22. The device of claim 1, wherein the membrane separates the chamber from the variable volume cavity.

23. The device of claim 1, wherein the membrane separates at least one of the inlet or the outlet from the variable volume cavity.

24. The device of claim 1, wherein the membrane is disposed between the container and the support member.

25. The device of claim 1, wherein the chamber is configured to utilize gravity to receive the bodily fluids from the inlet and to utilize gravity to prevent the bodily fluids from entering the outlet.

26. The device of claim 1, wherein the membrane is configured to prevent the passage of molecules that have a molecule size that is greater than a molecule size of the water-sized molecules.

27. The device of claim 26, wherein the molecule size that is greater than the water-sized molecules comprises at least one of sugar-sized molecules, protein-sized molecules, or microorganism-sized molecules.

28. The device of claim 1, wherein the water-sized molecules comprise solvent molecules.

29. The device of claim 1, wherein the tube is located external to the support member.

30. The device of claim 1, wherein the tube is in liquid communication with the dressing.

31. The device of claim 1, wherein the dressing comprises a drape configured to create a sealed space at the tissue site.

32. The device of claim 31, wherein the dressing comprises a tube adapter configured to be coupled to the drape and positioned in fluid communication between the sealed space and the tube.

33. The device of claim 31, wherein the membrane is hydrophilic.

34. The device of claim 1, wherein the support member comprises a porous filter configured to be in fluid communication between the inlet and the membrane.

* * * * *

UNITED STATES PATENT AND TRADEMARK OFFICE
CERTIFICATE OF CORRECTION

PATENT NO. : 10,857,268 B2
APPLICATION NO. : 14/173988
DATED : December 8, 2020
INVENTOR(S) : Robinson et al.

Page 1 of 1

It is certified that error appears in the above-identified patent and that said Letters Patent is hereby corrected as shown below:

On the Title Page

On Page 3, Column 2, Under (Other Publications)
Line 38, delete "Hypermia" and insert -- Hyperemia --, therefor.

In the Specification

Column 7
Line 4, after "form" delete "a".

In the Claims

Column 12
Line 45, in Claim 33, delete "claim 31," and insert -- claim 1, --, therefor.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*